(12) United States Patent
Nishiyama et al.

(10) Patent No.: US 6,187,311 B1
(45) Date of Patent: Feb. 13, 2001

(54) ENGINEERED ACARID ALLERGEN AND PROCESS FOR PRODUCING THE SAME

(75) Inventors: Chiharu Nishiyama; Toshifumi Yuuki; Yasushi Okumura, all of Outa-ku (JP)

(73) Assignees: Asahi Breweries, Ltd.; Torii Pharmaceuticals Co., Ltd.; The Nikka Whisky Distilling Co., Ltd., all of Tokyo (JP)

( * ) Notice: Under 35 U.S.C. 154(b), the term of this patent shall be extended for 0 days.

(21) Appl. No.: 08/930,264

(22) PCT Filed: Mar. 27, 1996

(86) PCT No.: PCT/JP96/00791

§ 371 Date: Sep. 26, 1997

§ 102(e) Date: Sep. 26, 1997

(87) PCT Pub. No.: WO96/30539

PCT Pub. Date: Oct. 3, 1996

(30) Foreign Application Priority Data

Mar. 28, 1995 (JP) ................................................. 7-093236

(51) Int. Cl.⁷ .......................... A61K 39/35; C07H 21/04; C12N 15/09; C12P 19/34
(52) U.S. Cl. .................... 424/191.1; 435/69.3; 435/91.1; 530/350; 536/23.5
(58) Field of Search ........................ 536/23.5; 435/320.1, 435/69.3, 91.1; 530/326, 324, 350; 424/191.1

(56) References Cited

U.S. PATENT DOCUMENTS 5,433,948 * 7/1995 Thomas .............................. 424/185.1
5,773,002 * 6/1998 Thomas .............................. 424/184.1
5,798,099 * 8/1998 Yuuki ................................. 424/185.1
5,876,722 * 3/1999 Yuuki ................................. 424/185.1

FOREIGN PATENT DOCUMENTS

06253851 * 9/1994 (JP) .
WO 92/04445 * 3/1992 (WO) .

OTHER PUBLICATIONS

Yuuki, T. et al., Cloning and expression of cDNA for the major house dust mite allergen Der f ii in *Escherichia coli,* Agric. Biol. Chem. 55(5):1233–1238, 1991.*

Trudinger, M., et al., cDNA encoding the major mite allergen Der f ii. Clin. Exp. Allerg. 21:33–37, 1991.*

Yuuki, T., et al., Synthesis of biologically acitve recombinant Der f II. Int. Arch. Appl. Immunol. 94:354–356, 1991.*

Naeve, CW., et al., Accuracy of automated DNA sequencing: a multi-laboratory comparison of sequencing results. Biotechniques. 19(3):448–453, 1995.*

* cited by examiner

*Primary Examiner*—David Saunders
*Assistant Examiner*—Mary Beth Tung
(74) *Attorney, Agent, or Firm*—Browdy And Neimark

(57) ABSTRACT

The invention provides a method for producing a modified major mite allergen, obtained by altering a major allergen of house dust mites by gene engineering, which involve the steps of culturing prokaryotic or eukaryotic host cells transformed with a replication vector containing a gene encoding modified major mite allergen expressed from a promoter and collecting the expressed modified major mite allergen from the culture. The present invention provides a modified major mite allergen produced by the method, DNA molecules encoding same, and a pharmaceutical composition containing the modified major mite allergen.

6 Claims, 2 Drawing Sheets

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
      (A) LENGTH: 390 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..387

(xi) SEQUENCE DESCRIPTION: SEQ ID NO:1:

```
GAT CAA GTC GAT GTT AAA GAT TGT GCC AAC AAT GAA ATC AAA AAA GTA        48
Asp Gln Val Asp Val Lys Asp Cys Ala Asn Asn Glu Ile Lys Lys Val
 1               5                  10                  15

ATG GTC GAT GGT TGC CAT GGT TCT GAT CCA TGC ATC ATC CAT CGT GGT        96
Met Val Asp Gly Cys His Gly Ser Asp Pro Cys Ile Ile His Arg Gly
                20                  25                  30

AAA CCA TTC ACT TTG GAA GCC TTA TTC GAT GCC AAC CAA AAC ACT AAA       144
Lys Pro Phe Thr Leu Glu Ala Leu Phe Asp Ala Asn Gln Asn Thr Lys
            35                  40                  45

ACC GCT AAA ATT GAA ATC AAA GCC AGC CTC GAT GGT CTT GAA ATT GAT       192
Thr Ala Lys Ile Glu Ile Lys Ala Ser Leu Asp Gly Leu Glu Ile Asp
        50                  55                  60

GTT CCC GGT ATC GAT ACC AAT GCT TGC CAT TTT GTC AAA TGT CCA TTG       240
Val Pro Gly Ile Asp Thr Asn Ala Cys His Phe Val Lys Cys Pro Leu
 65                  70                  75                  80

GTT AAA GGT CAA CAA TAT GAT ATC AAA TAT ACA TGG AAT GTG CCG AAA       288
Val Lys Gly Gln Gln Tyr Asp Ile Lys Tyr Thr Trp Asn Val Pro Lys
```

-continued

```
                85                   90                   95
ATT GCA CCA AAA TCT GAA AAC GTT GTC GTT ACA GTC AAA CTT ATC GGT      336
Ile Ala Pro Lys Ser Glu Asn Val Val Val Thr Val Lys Leu Ile Gly
            100                 105                 110

GAT AAT GGT GTT TTG GCT TGC GCT ATT GCT ACC CAC GGT AAA ATC CGT      384
Asp Asn Gly Val Leu Ala Cys Ala Ile Ala Thr His Gly Lys Ile Arg
        115                 120                 125

GAT TAA                                                              390
Asp
```

(2) INFORMATION FOR SEQ ID NO:2:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO:2:

```
Asp Gln Val Asp Val Lys Asp Cys Ala Asn Asn Glu Ile Lys Lys Val
 1               5                  10                  15

Met Val Asp Gly Cys His Gly Ser Asp Pro Cys Ile Ile His Arg Gly
            20                  25                  30

Lys Pro Phe Thr Leu Glu Ala Leu Phe Asp Ala Asn Gln Asn Thr Lys
        35                  40                  45

Thr Ala Lys Ile Glu Ile Lys Ala Ser Leu Asp Gly Leu Glu Ile Asp
    50                  55                  60

Val Pro Gly Ile Asp Thr Asn Ala Cys His Phe Val Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Leu Ile Gly
            100                 105                 110

Asp Asn Gly Val Leu Ala Cys Ala Ile Ala Thr His Gly Lys Ile Arg
        115                 120                 125

Asp
```

(2) INFORMATION FOR SEQ ID NO:3:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..387

(xi) SEQUENCE DESCRIPTION: SEQ ID NO:3:

```
GAT CAA GTC GAT GTT AAA GAT TGT GCC AAC AAT GAA ATC AAA AAA GTA       48
Asp Gln Val Asp Val Lys Asp Cys Ala Asn Asn Glu Ile Lys Lys Val
130                 135                 140                 145

ATG GTC GAT GGT TGC CAT GGT TCT GAT CCA TGC ATC ATC CAT CGT GGT       96
Met Val Asp Gly Cys His Gly Ser Asp Pro Cys Ile Ile His Arg Gly
                150                 155                 160

AAA CCA TTC ACT TTG GAA GCC TTA TTC GAT GCC AAC CAA AAC ACT AAA      144
Lys Pro Phe Thr Leu Glu Ala Leu Phe Asp Ala Asn Gln Asn Thr Lys
            165                 170                 175
```

```
ACC GCT AAA ATT GAA ATC AAA GCC AGC CTC GAT GGT CTT GAA ATT GAT      192
Thr Ala Lys Ile Glu Ile Lys Ala Ser Leu Asp Gly Leu Glu Ile Asp
            180                 185                 190

GTT CCC GGT ATC GAT ACC AAT GCT TGC CAT TTT ATG AAA TGT CCA TTG      240
Val Pro Gly Ile Asp Thr Asn Ala Cys His Phe Met Lys Cys Pro Leu
195                 200                 205

GTT AAA GGT CAA CAA TAT GAT ATC AAA TAT ACA TGG AAT GTG CCG AAA      288
Val Lys Gly Gln Gln Tyr Asp Ile Lys Tyr Thr Trp Asn Val Pro Lys
210                 215                 220                 225

ATT GCA CCA AAA TCT GAA AAC GTT GTC GTT ACA GTC AAA CTT ATC GGT      336
Ile Ala Pro Lys Ser Glu Asn Val Val Val Thr Val Lys Leu Ile Gly
            230                 235                 240

GAT AAT GGT GTT TTG GCT TGC GCT ATT GCT ACC CAC GGT AAA ATC CGT      384
Asp Asn Gly Val Leu Ala Cys Ala Ile Ala Thr His Gly Lys Ile Arg
            245                 250                 255

GAT TAA                                                              390
Asp
```

(2) INFORMATION FOR SEQ ID NO:4:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO:4:

```
Asp Gln Val Asp Val Lys Asp Cys Ala Asn Asn Glu Ile Lys Lys Val
1               5                   10                  15

Met Val Asp Gly Cys His Gly Ser Asp Pro Cys Ile Ile His Arg Gly
                20                  25                  30

Lys Pro Phe Thr Leu Glu Ala Leu Phe Asp Ala Asn Gln Asn Thr Lys
            35                  40                  45

Thr Ala Lys Ile Glu Ile Lys Ala Ser Leu Asp Gly Leu Glu Ile Asp
    50                  55                  60

Val Pro Gly Ile Asp Thr Asn Ala Cys His Phe Met Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Leu Ile Gly
            100                 105                 110

Asp Asn Gly Val Leu Ala Cys Ala Ile Ala Thr His Gly Lys Ile Arg
    115                 120                 125

Asp
```

(2) INFORMATION FOR SEQ ID NO:5:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..387

(xi) SEQUENCE DESCRIPTION: SEQ ID NO:5:

-continued

```
GAT CAA GTC GAT GTT AAA GAT TGT GCC AAC AAT GAA ATC AAA AAA GTA        48
Asp Gln Val Asp Val Lys Asp Cys Ala Asn Asn Glu Ile Lys Lys Val
130             135                 140                 145

ATG GTC GAT GGT TGC CAT GGT TCT GAT CCA TGC ATC ATC CAT CGT GGT        96
Met Val Asp Gly Cys His Gly Ser Asp Pro Cys Ile Ile His Arg Gly
                150                 155                 160

AAA CCA TTC ACT TTG GAA GCC TTA TTC GAT GCC AAC CAA AAC ACT AAA       144
Lys Pro Phe Thr Leu Glu Ala Leu Phe Asp Ala Asn Gln Asn Thr Lys
            165                 170                 175

ACC GCT AAA ATT GAA ATC AAA GCC AGC CTC GAT GGT CTT GAA ATT GAT       192
Thr Ala Lys Ile Glu Ile Lys Ala Ser Leu Asp Gly Leu Glu Ile Asp
        180                 185                 190

GTT CCC GGT ATC GAT ACC AAT GCT TGC CAT TTT ATG AAA TGT CCA TTG       240
Val Pro Gly Ile Asp Thr Asn Ala Cys His Phe Met Lys Cys Pro Leu
    195                 200                 205

GTT AAA GGT CAA CAA TAT GAT GCC AAA TAT ACA TGG AAT GTG CCG AAA       288
Val Lys Gly Gln Gln Tyr Asp Ala Lys Tyr Thr Trp Asn Val Pro Lys
210                 215                 220                 225

ATT GCA CCA AAA TCT GAA AAC GTT GTC GTT ACA GTC AAA CTT GTT GGT       336
Ile Ala Pro Lys Ser Glu Asn Val Val Val Thr Val Lys Leu Val Gly
                230                 235                 240

GAT AAT GGT GTT TTG GCT TGC GCT ATT GCT ACC CAC GCT AAA ATC CGT       384
Asp Asn Gly Val Leu Ala Cys Ala Ile Ala Thr His Ala Lys Ile Arg
            245                 250                 255

GAT TAA                                                                390
Asp
```

(2) INFORMATION FOR SEQ ID NO:6:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO:6:

```
Asp Gln Val Asp Val Lys Asp Cys Ala Asn Asn Glu Ile Lys Lys Val
 1               5                  10                  15

Met Val Asp Gly Cys His Gly Ser Asp Pro Cys Ile Ile His Arg Gly
                20                  25                  30

Lys Pro Phe Thr Leu Glu Ala Leu Phe Asp Ala Asn Gln Asn Thr Lys
            35                  40                  45

Thr Ala Lys Ile Glu Ile Lys Ala Ser Leu Asp Gly Leu Glu Ile Asp
        50                  55                  60

Val Pro Gly Ile Asp Thr Asn Ala Cys His Phe Met Lys Cys Pro Leu
65                  70                  75                  80

Val Lys Gly Gln Gln Tyr Asp Ala Lys Tyr Thr Trp Asn Val Pro Lys
                85                  90                  95

Ile Ala Pro Lys Ser Glu Asn Val Val Val Thr Val Lys Leu Val Gly
            100                 105                 110

Asp Asn Gly Val Leu Ala Cys Ala Ile Ala Thr His Ala Lys Ile Arg
        115                 120                 125

Asp
```

(2) INFORMATION FOR SEQ ID NO:7:

(i) SEQUENCE CHARACTERISTICS:
        (A) LENGTH: 390 base pairs
        (B) TYPE: nucleic acid

```
          (C) STRANDEDNESS: single
          (D) TOPOLOGY: linear (ii) MOLECULE TYPE: cDNA (ix) FEATURE:
          (A) NAME/KEY: CDS
          (B) LOCATION: 1..387

(xi) SEQUENCE DESCRIPTION: SEQ ID NO:7:

GAT CAA GTC GAT GTT AAA GAG TGT GCC AAC AAT GAA ATC AAA AAA GTA        48
Asp Gln Val Asp Val Lys Glu Cys Ala Asn Asn Glu Ile Lys Lys Val
130             135                 140                 145

ATG GTC GAT GGT TGC CAT GGT TCT GAT CCA TGC ATC ATC CAT CGT GGT        96
Met Val Asp Gly Cys His Gly Ser Asp Pro Cys Ile Ile His Arg Gly
                150                 155                 160

AAA CCA TTC ACT TTG GAA GCC TTA TTC GAT GCC AAC CAA AAC ACT AAA       144
Lys Pro Phe Thr Leu Glu Ala Leu Phe Asp Ala Asn Gln Asn Thr Lys
            165                 170                 175

ACC GCT AAA ATT GAA ATC AAA GCC AGC CTC GAT GGT CTT GAA ATT GAT       192
Thr Ala Lys Ile Glu Ile Lys Ala Ser Leu Asp Gly Leu Glu Ile Asp
        180                 185                 190

GTT CCC GGT ATC GAT ACC AAT GCT TGC CAT TTT ATG AAA TGT CCA TTG       240
Val Pro Gly Ile Asp Thr Asn Ala Cys His Phe Met Lys Cys Pro Leu
    195                 200                 205

GTT AAA GGT CAA CAA TAT GAT GCC AAA TAT ACA TGG AAT GTG CCG AAA       288
Val Lys Gly Gln Gln Tyr Asp Ala Lys Tyr Thr Trp Asn Val Pro Lys
210                 215                 220                 225

ATT GCA CCA AAA TCT GAA AAC GTT GTC GTT ACA GTC AAA CTT GTT GGT       336
Ile Ala Pro Lys Ser Glu Asn Val Val Val Thr Val Lys Leu Val Gly
                230                 235                 240

GAT AAT GGT GTT TTG GCT TGC GCT ATT GCT ACC CAC GCT AAA ATC CGT       384
Asp Asn Gly Val Leu Ala Cys Ala Ile Ala Thr His Ala Lys Ile Arg
            245                 250                 255

GAT TAA                                                               390
Asp (2) INFORMATION FOR SEQ ID NO:8:

(i) SEQUENCE CHARACTERISTICS:
          (A) LENGTH: 129 amino acids
          (B) TYPE: amino acid
          (D) TOPOLOGY: linear (ii) MOLECULE TYPE: protein (xi) SEQUENCE DESCRIPTION: SEQ ID NO:8:

Asp Gln Val Asp Val Lys Glu Cys Ala Asn Asn Glu Ile Lys Lys Val
1               5                   10                  15

Met Val Asp Gly Cys His Gly Ser Asp Pro Cys Ile Ile His Arg Gly
                20                  25                  30

Lys Pro Phe Thr Leu Glu Ala Leu Phe Asp Ala Asn Gln Asn Thr Lys
            35                  40                  45

Thr Ala Lys Ile Glu Ile Lys Ala Ser Leu Asp Gly Leu Glu Ile Asp
        50                  55                  60

Val Pro Gly Ile Asp Thr Asn Ala Cys His Phe Met Lys Cys Pro Leu
65                  70                  75                  80

Val Lys Gly Gln Gln Tyr Asp Ala Lys Tyr Thr Trp Asn Val Pro Lys
                85                  90                  95

Ile Ala Pro Lys Ser Glu Asn Val Val Val Thr Val Lys Leu Val Gly
            100                 105                 110
```

```
Asp Asn Gly Val Leu Ala Cys Ala Ile Ala Thr His Ala Lys Ile Arg
        115                 120                 125

Asp
```

(2) INFORMATION FOR SEQ ID NO:9:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..387

(xi) SEQUENCE DESCRIPTION: SEQ ID NO:9:

```
GAT CAA GTC GAT GTT AAA AAT TGT GCC AAC AAT GAA ATC AAA AAA GTA    48
Asp Gln Val Asp Val Lys Asn Cys Ala Asn Asn Glu Ile Lys Lys Val
130             135                 140                 145

ATG GTC GAT GGT TGC CAT GGT TCT GAT CCA TGC ATC ATC CAT CGT GGT    96
Met Val Asp Gly Cys His Gly Ser Asp Pro Cys Ile Ile His Arg Gly
            150                 155                 160

AAA CCA TTC ACT TTG GAA GCC TTA TTC GAT GCC AAC CAA AAC ACT AAA   144
Lys Pro Phe Thr Leu Glu Ala Leu Phe Asp Ala Asn Gln Asn Thr Lys
        165                 170                 175

ACC GCT AAA ATT GAA ATC AAA GCC AGC CTC GAT GGT CTT GAA ATT GAT   192
Thr Ala Lys Ile Glu Ile Lys Ala Ser Leu Asp Gly Leu Glu Ile Asp
            180                 185                 190

GTT CCC GGT ATC GAT ACC AAT GCT TGC CAT TTT ATG AAA TGT CCA TTG   240
Val Pro Gly Ile Asp Thr Asn Ala Cys His Phe Met Lys Cys Pro Leu
195                 200                 205

GTT AAA GGT CAA CAA TAT GAT GCC AAA TAT ACA TGG AAT GTG CCG AAA   288
Val Lys Gly Gln Gln Tyr Asp Ala Lys Tyr Thr Trp Asn Val Pro Lys
210                 215                 220                 225

ATT GCA CCA AAA TCT GAA AAC GTT GTC GTT ACA GTC AAA CTT GTT GGT   336
Ile Ala Pro Lys Ser Glu Asn Val Val Val Thr Val Lys Leu Val Gly
                230                 235                 240

GAT AAT GGT GTT TTG GCT TGC GCT ATT GCT ACC CAC GCT AAA ATC CGT   384
Asp Asn Gly Val Leu Ala Cys Ala Ile Ala Thr His Ala Lys Ile Arg
            245                 250                 255

GAT TAA                                                            390
Asp
```

(2) INFORMATION FOR SEQ ID NO:10:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO:10:

```
Asp Gln Val Asp Val Lys Asn Cys Ala Asn Asn Glu Ile Lys Lys Val
1               5                   10                  15

Met Val Asp Gly Cys His Gly Ser Asp Pro Cys Ile Ile His Arg Gly
            20                  25                  30

Lys Pro Phe Thr Leu Glu Ala Leu Phe Asp Ala Asn Gln Asn Thr Lys
        35                  40                  45

Thr Ala Lys Ile Glu Ile Lys Ala Ser Leu Asp Gly Leu Glu Ile Asp
```

```
                   50                      55                      60
Val Pro Gly Ile Asp Thr Asn Ala Cys His Phe Met Lys Cys Pro Leu
 65                      70                      75                      80

Val Lys Gly Gln Gln Tyr Asp Ala Lys Tyr Thr Trp Asn Val Pro Lys
                         85                      90                      95

Ile Ala Pro Lys Ser Glu Asn Val Val Val Thr Val Lys Leu Val Gly
                    100                     105                     110

Asp Asn Gly Val Leu Ala Cys Ala Ile Ala Thr His Ala Lys Ile Arg
               115                     120                     125

Asp
```

(2) INFORMATION FOR SEQ ID NO:11:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..387

(xi) SEQUENCE DESCRIPTION: SEQ ID NO:11:

```
GAT CAA GTC GAT GTT AAA AAA TGT GCC AAC AAT GAA ATC AAA AAA GTA        48
Asp Gln Val Asp Val Lys Lys Cys Ala Asn Asn Glu Ile Lys Lys Val
130                     135                     140                     145

ATG GTC GAT GGT TGC CAT GGT TCT GAT CCA TGC ATC ATC CAT CGT GGT        96
Met Val Asp Gly Cys His Gly Ser Asp Pro Cys Ile Ile His Arg Gly
                    150                     155                     160

AAA CCA TTC ACT TTG GAA GCC TTA TTC GAT GCC AAC CAA AAC ACT AAA       144
Lys Pro Phe Thr Leu Glu Ala Leu Phe Asp Ala Asn Gln Asn Thr Lys
               165                     170                     175

ACC GCT AAA ATT GAA ATC AAA GCC AGC CTC GAT GGT CTT GAA ATT GAT       192
Thr Ala Lys Ile Glu Ile Lys Ala Ser Leu Asp Gly Leu Glu Ile Asp
          180                     185                     190

GTT CCC GGT ATC GAT ACC AAT GCT TGC CAT TTT ATG AAA TGT CCA TTG       240
Val Pro Gly Ile Asp Thr Asn Ala Cys His Phe Met Lys Cys Pro Leu
195                     200                     205

GTT AAA GGT CAA CAA TAT GAT GCC AAA TAT ACA TGG AAT GTG CCG AAA       288
Val Lys Gly Gln Gln Tyr Asp Ala Lys Tyr Thr Trp Asn Val Pro Lys
210                     215                     220                     225

ATT GCA CCA AAA TCT GAA AAC GTT GTC GTT ACA GTC AAA CTT GTT GGT       336
Ile Ala Pro Lys Ser Glu Asn Val Val Val Thr Val Lys Leu Val Gly
                    230                     235                     240

GAT AAT GGT GTT TTG GCT TGC GCT ATT GCT ACC CAC GCT AAA ATC CGT       384
Asp Asn Gly Val Leu Ala Cys Ala Ile Ala Thr His Ala Lys Ile Arg
               245                     250                     255

GAT TAA                                                                390
Asp
```

(2) INFORMATION FOR SEQ ID NO:12:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO:12:

```
Asp Gln Val Asp Val Lys Lys Cys Ala Asn Asn Glu Ile Lys Lys Val
 1               5                  10                  15

Met Val Asp Gly Cys His Gly Ser Asp Pro Cys Ile Ile His Arg Gly
             20                  25                  30

Lys Pro Phe Thr Leu Glu Ala Leu Phe Asp Ala Asn Gln Asn Thr Lys
         35                  40                  45

Thr Ala Lys Ile Glu Ile Lys Ala Ser Leu Asp Gly Leu Glu Ile Asp
     50                  55                  60

Val Pro Gly Ile Asp Thr Asn Ala Cys His Phe Met Lys Cys Pro Leu
 65              70                  75                  80

Val Lys Gly Gln Gln Tyr Asp Ala Lys Tyr Thr Trp Asn Val Pro Lys
             85                  90                  95

Ile Ala Pro Lys Ser Glu Asn Val Val Val Thr Val Lys Leu Val Gly
            100                 105                 110

Asp Asn Gly Val Leu Ala Cys Ala Ile Ala Thr His Ala Lys Ile Arg
            115                 120                 125

Asp
```

(2) INFORMATION FOR SEQ ID NO:13:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..387

(xi) SEQUENCE DESCRIPTION: SEQ ID NO:13:

```
GAT CAA GTC GAT GTT AAA GAT TGT CCC AAC AAT GAA ATC AAA AAA GTA      48
Asp Gln Val Asp Val Lys Asp Cys Pro Asn Asn Glu Ile Lys Lys Val
130              135                 140                 145

ATG GTC GAT GGT TGC CAT GGT TCT GAT CCA TGC ATC ATC CAT CGT GGT      96
Met Val Asp Gly Cys His Gly Ser Asp Pro Cys Ile Ile His Arg Gly
             150                 155                 160

AAA CCA TTC ACT TTG GAA GCC TTA TTC GAT GCC AAC CAA AAC ACT AAA     144
Lys Pro Phe Thr Leu Glu Ala Leu Phe Asp Ala Asn Gln Asn Thr Lys
         165                 170                 175

ACC GCT AAA ATT GAA ATC AAA GCC AGC CTC GAT GGT CTT GAA ATT GAT     192
Thr Ala Lys Ile Glu Ile Lys Ala Ser Leu Asp Gly Leu Glu Ile Asp
     180                 185                 190

GTT CCC GGT ATC GAT ACC AAT GCT TGC CAT TTT ATG AAA TGT CCA TTG     240
Val Pro Gly Ile Asp Thr Asn Ala Cys His Phe Met Lys Cys Pro Leu
 195                 200                 205

GTT AAA GGT CAA CAA TAT GAT GCC AAA TAT ACA TGG AAT GTG CCG AAA     288
Val Lys Gly Gln Gln Tyr Asp Ala Lys Tyr Thr Trp Asn Val Pro Lys
210                 215                 220                 225

ATT GCA CCA AAA TCT GAA AAC GTT GTC GTT ACA GTC AAA CTT GTT GGT     336
Ile Ala Pro Lys Ser Glu Asn Val Val Val Thr Val Lys Leu Val Gly
                230                 235                 240

GAT AAT GGT GTT TTG GCT TGC GCT ATT GCT ACC CAC GCT AAA ATC CGT     384
Asp Asn Gly Val Leu Ala Cys Ala Ile Ala Thr His Ala Lys Ile Arg
            245                 250                 255

GAT TAA                                                              390
Asp
```

(2) INFORMATION FOR SEQ ID NO:14:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO:14:

```
Asp Gln Val Asp Val Lys Asp Cys Pro Asn Asn Glu Ile Lys Lys Val
 1               5                  10                  15

Met Val Asp Gly Cys His Gly Ser Asp Pro Cys Ile Ile His Arg Gly
            20                  25                  30

Lys Pro Phe Thr Leu Glu Ala Leu Phe Asp Ala Asn Gln Asn Thr Lys
        35                  40                  45

Thr Ala Lys Ile Glu Ile Lys Ala Ser Leu Asp Gly Leu Glu Ile Asp
    50                  55                  60

Val Pro Gly Ile Asp Thr Asn Ala Cys His Phe Met Lys Cys Pro Leu
65                  70                  75                  80

Val Lys Gly Gln Gln Tyr Asp Ala Lys Tyr Thr Trp Asn Val Pro Lys
            85                  90                  95

Ile Ala Pro Lys Ser Glu Asn Val Val Val Thr Val Lys Leu Val Gly
        100                 105                 110

Asp Asn Gly Val Leu Ala Cys Ala Ile Ala Thr His Ala Lys Ile Arg
    115                 120                 125

Asp
```

(2) INFORMATION FOR SEQ ID NO:15:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..387

(xi) SEQUENCE DESCRIPTION: SEQ ID NO:15:

```
GAT CAA GTC GAT GTT AAA GAT TGT GCC AAC AAT GAA ATC AAA AAA GTA    48
Asp Gln Val Asp Val Lys Asp Cys Ala Asn Asn Glu Ile Lys Lys Val
130             135                 140                 145

ATG GTC GAA GGT TGC CAT GGT TCT GAT CCA TGC ATC ATC CAT CGT GGT    96
Met Val Glu Gly Cys His Gly Ser Asp Pro Cys Ile Ile His Arg Gly
            150                 155                 160

AAA CCA TTC ACT TTG GAA GCC TTA TTC GAT GCC AAC CAA AAC ACT AAA   144
Lys Pro Phe Thr Leu Glu Ala Leu Phe Asp Ala Asn Gln Asn Thr Lys
        165                 170                 175

ACC GCT AAA ATT GAA ATC AAA GCC AGC CTC GAT GGT CTT GAA ATT GAT   192
Thr Ala Lys Ile Glu Ile Lys Ala Ser Leu Asp Gly Leu Glu Ile Asp
    180                 185                 190

GTT CCC GGT ATC GAT ACC AAT GCT TGC CAT TTT ATG AAA TGT CCA TTG   240
Val Pro Gly Ile Asp Thr Asn Ala Cys His Phe Met Lys Cys Pro Leu
    195                 200                 205

GTT AAA GGT CAA CAA TAT GAT GCC AAA TAT ACA TGG AAT GTG CCG AAA   288
Val Lys Gly Gln Gln Tyr Asp Ala Lys Tyr Thr Trp Asn Val Pro Lys
210                 215                 220                 225
```

```
ATT GCA CCA AAA TCT GAA AAC GTT GTC GTT ACA GTC AAA CTT GTT GGT        336
Ile Ala Pro Lys Ser Glu Asn Val Val Val Thr Val Lys Leu Val Gly
            230                 235                 240

GAT AAT GGT GTT TTG GCT TGC GCT ATT GCT ACC CAC GCT AAA ATC CGT        384
Asp Asn Gly Val Leu Ala Cys Ala Ile Ala Thr His Ala Lys Ile Arg
            245                 250                 255

GAT TAA                                                                 390
Asp
```

(2) INFORMATION FOR SEQ ID NO:16:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO:16:

```
Asp Gln Val Asp Val Lys Asp Cys Ala Asn Asn Glu Ile Lys Lys Val
 1               5                  10                  15

Met Val Glu Gly Cys His Gly Ser Asp Pro Cys Ile Ile His Arg Gly
            20                  25                  30

Lys Pro Phe Thr Leu Glu Ala Leu Phe Asp Ala Asn Gln Asn Thr Lys
            35                  40                  45

Thr Ala Lys Ile Glu Ile Lys Ala Ser Leu Asp Gly Leu Glu Ile Asp
        50                  55                  60

Val Pro Gly Ile Asp Thr Asn Ala Cys His Phe Met Lys Cys Pro Leu
 65                  70                  75                  80

Val Lys Gly Gln Gln Tyr Asp Ala Lys Tyr Thr Trp Asn Val Pro Lys
                85                  90                  95

Ile Ala Pro Lys Ser Glu Asn Val Val Val Thr Val Lys Leu Val Gly
            100                 105                 110

Asp Asn Gly Val Leu Ala Cys Ala Ile Ala Thr His Ala Lys Ile Arg
            115                 120                 125

Asp
```

(2) INFORMATION FOR SEQ ID NO:17:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..387

(xi) SEQUENCE DESCRIPTION: SEQ ID NO:17:

```
GAT CAA GTC GAT GTT AAA GAT TGT GCC AAC AAT GAA ATC AAA AAA GTA         48
Asp Gln Val Asp Val Lys Asp Cys Ala Asn Asn Glu Ile Lys Lys Val
130                 135                 140                 145

ATG GTC AAC GGT TGC CAT GGT TCT GAT CCA TGC ATC ATC CAT CGT GGT         96
Met Val Asn Gly Cys His Gly Ser Asp Pro Cys Ile Ile His Arg Gly
            150                 155                 160

AAA CCA TTC ACT TTG GAA GCC TTA TTC GAT GCC AAC CAA AAC ACT AAA        144
Lys Pro Phe Thr Leu Glu Ala Leu Phe Asp Ala Asn Gln Asn Thr Lys
            165                 170                 175

ACC GCT AAA ATT GAA ATC AAA GCC AGC CTC GAT GGT CTT GAA ATT GAT        192
```

```
Thr Ala Lys Ile Glu Ile Lys Ala Ser Leu Asp Gly Leu Glu Ile Asp
        180                 185                 190

GTT CCC GGT ATC GAT ACC AAT GCT TGC CAT TTT ATG AAA TGT CCA TTG      240
Val Pro Gly Ile Asp Thr Asn Ala Cys His Phe Met Lys Cys Pro Leu
195                 200                 205

GTT AAA GGT CAA CAA TAT GAT GCC AAA TAT ACA TGG AAT GTG CCG AAA      288
Val Lys Gly Gln Gln Tyr Asp Ala Lys Tyr Thr Trp Asn Val Pro Lys
210                 215                 220                 225

ATT GCA CCA AAA TCT GAA AAC GTT GTC GTT ACA GTC AAA CTT GTT GGT      336
Ile Ala Pro Lys Ser Glu Asn Val Val Val Thr Val Lys Leu Val Gly
                230                 235                 240

GAT AAT GGT GTT TTG GCT TGC GCT ATT GCT ACC CAC GCT AAA ATC CGT      384
Asp Asn Gly Val Leu Ala Cys Ala Ile Ala Thr His Ala Lys Ile Arg
            245                 250                 255

GAT TAA                                                              390
Asp (2) INFORMATION FOR SEQ ID NO:18:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO:18:

Asp Gln Val Asp Val Lys Asp Cys Ala Asn Asn Glu Ile Lys Lys Val
 1               5                  10                  15

Met Val Asn Gly Cys His Gly Ser Asp Pro Cys Ile Ile His Arg Gly
            20                  25                  30

Lys Pro Phe Thr Leu Glu Ala Leu Phe Asp Ala Asn Gln Asn Thr Lys
        35                  40                  45

Thr Ala Lys Ile Glu Ile Lys Ala Ser Leu Asp Gly Leu Glu Ile Asp
    50                  55                  60

Val Pro Gly Ile Asp Thr Asn Ala Cys His Phe Met Lys Cys Pro Leu
65                  70                  75                  80

Val Lys Gly Gln Gln Tyr Asp Ala Lys Tyr Thr Trp Asn Val Pro Lys
                85                  90                  95

Ile Ala Pro Lys Ser Glu Asn Val Val Val Thr Val Lys Leu Val Gly
            100                 105                 110

Asp Asn Gly Val Leu Ala Cys Ala Ile Ala Thr His Ala Lys Ile Arg
        115                 120                 125

Asp (2) INFORMATION FOR SEQ ID NO:19:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..387

(xi) SEQUENCE DESCRIPTION: SEQ ID NO:19:

GAT CAA GTC GAT GTT AAA GAT TGT GCC AAC AAT GAA ATC AAA AAA GTA       48
Asp Gln Val Asp Val Lys Asp Cys Ala Asn Asn Glu Ile Lys Lys Val
```

```
                130              135              140              145
ATG GTC AAA GGT TGC CAT GGT TCT GAT CCA TGC ATC ATC CAT CGT GGT      96
Met Val Lys Gly Cys His Gly Ser Asp Pro Cys Ile Ile His Arg Gly
                150              155              160

AAA CCA TTC ACT TTG GAA GCC TTA TTC GAT GCC AAC CAA AAC ACT AAA     144
Lys Pro Phe Thr Leu Glu Ala Leu Phe Asp Ala Asn Gln Asn Thr Lys
                165              170              175

ACC GCT AAA ATT GAA ATC AAA GCC AGC CTC GAT GGT CTT GAA ATT GAT     192
Thr Ala Lys Ile Glu Ile Lys Ala Ser Leu Asp Gly Leu Glu Ile Asp
                180              185              190

GTT CCC GGT ATC GAT ACC AAT GCT TGC CAT TTT ATG AAA TGT CCA TTG     240
Val Pro Gly Ile Asp Thr Asn Ala Cys His Phe Met Lys Cys Pro Leu
    195              200              205

GTT AAA GGT CAA CAA TAT GAT GCC AAA TAT ACA TGG AAT GTG CCG AAA     288
Val Lys Gly Gln Gln Tyr Asp Ala Lys Tyr Thr Trp Asn Val Pro Lys
210              215              220              225

ATT GCA CCA AAA TCT GAA AAC GTT GTC GTT ACA GTC AAA CTT GTT GGT     336
Ile Ala Pro Lys Ser Glu Asn Val Val Val Thr Val Lys Leu Val Gly
                230              235              240

GAT AAT GGT GTT TTG GCT TGC GCT ATT GCT ACC CAC GCT AAA ATC CGT     384
Asp Asn Gly Val Leu Ala Cys Ala Ile Ala Thr His Ala Lys Ile Arg
                245              250              255

GAT TAA                                                             390
Asp
```

(2) INFORMATION FOR SEQ ID NO:20:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO:20:

```
Asp Gln Val Asp Val Lys Asp Cys Ala Asn Asn Glu Ile Lys Lys Val
 1               5                   10                  15

Met Val Lys Gly Cys His Gly Ser Asp Pro Cys Ile Ile His Arg Gly
                20                  25                  30

Lys Pro Phe Thr Leu Glu Ala Leu Phe Asp Ala Asn Gln Asn Thr Lys
                35                  40                  45

Thr Ala Lys Ile Glu Ile Lys Ala Ser Leu Asp Gly Leu Glu Ile Asp
        50                  55                  60

Val Pro Gly Ile Asp Thr Asn Ala Cys His Phe Met Lys Cys Pro Leu
65              70                  75                  80

Val Lys Gly Gln Gln Tyr Asp Ala Lys Tyr Thr Trp Asn Val Pro Lys
                85                  90                  95

Ile Ala Pro Lys Ser Glu Asn Val Val Val Thr Val Lys Leu Val Gly
                100                 105                 110

Asp Asn Gly Val Leu Ala Cys Ala Ile Ala Thr His Ala Lys Ile Arg
            115                 120                 125

Asp
```

(2) INFORMATION FOR SEQ ID NO:21:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: cDNA (ix) FEATURE:
             (A) NAME/KEY: CDS
             (B) LOCATION: 1..387

(xi) SEQUENCE DESCRIPTION: SEQ ID NO:21:

```
GAT CAA GTC GAT GTT AAA GAT TGT GCC AAC AAT GAA ATC AAA AAA GTA         48
Asp Gln Val Asp Val Lys Asp Cys Ala Asn Asn Glu Ile Lys Lys Val
130             135                 140                 145

ATG GTC GAT GGT TGC CAT GGT TCT GAT CCA TGC ATC ATC CAT CGT GGT         96
Met Val Asp Gly Cys His Gly Ser Asp Pro Cys Ile Ile His Arg Gly
                150                 155                 160

AAA CCA TTC ACT TTG GAA GCC TTA TTC GAT GCC AAC CAA AAC ACT AAA        144
Lys Pro Phe Thr Leu Glu Ala Leu Phe Asp Ala Asn Gln Asn Thr Lys
                165                 170                 175

ACC GCT AAA ATT GAA ATC AAA GCC AGC CTC GAT GGT CTT GAA ATT GAT        192
Thr Ala Lys Ile Glu Ile Lys Ala Ser Leu Asp Gly Leu Glu Ile Asp
                180                 185                 190

GTT CCC GGT ATC GAT ACC AAT GCT TGC CAT TTT ATG AAA TGT CCA TTG        240
Val Pro Gly Ile Asp Thr Asn Ala Cys His Phe Met Lys Cys Pro Leu
    195                 200                 205

GTT AAA GGT CAA CAA TAT GAT GCC AAA TAT ACA TGG AAT GTG CCG AAA        288
Val Lys Gly Gln Gln Tyr Asp Ala Lys Tyr Thr Trp Asn Val Pro Lys
210                 215                 220                 225

ATT GCA CCA AAA TCT GAA AAC GTT GTC GTT ACA GTC AAA CTT GTT GGT        336
Ile Ala Pro Lys Ser Glu Asn Val Val Val Thr Val Lys Leu Val Gly
                230                 235                 240

GAT AAT GGT GTT TTG GCT TGC GCT ATT GCT ACC CAC GCT AAA ATC GAT        384
Asp Asn Gly Val Leu Ala Cys Ala Ile Ala Thr His Ala Lys Ile Asp
                245                 250                 255

GAT TAA                                                                 390
Asp
```

(2) INFORMATION FOR SEQ ID NO:22:

(i) SEQUENCE CHARACTERISTICS:
             (A) LENGTH: 129 amino acids
             (B) TYPE: amino acid
             (D) TOPOLOGY: linear (ii) MOLECULE TYPE: protein (xi) SEQUENCE DESCRIPTION: SEQ ID NO:22:

```
Asp Gln Val Asp Val Lys Asp Cys Ala Asn Asn Glu Ile Lys Lys Val
 1               5                  10                  15

Met Val Asp Gly Cys His Gly Ser Asp Pro Cys Ile Ile His Arg Gly
                20                  25                  30

Lys Pro Phe Thr Leu Glu Ala Leu Phe Asp Ala Asn Gln Asn Thr Lys
                35                  40                  45

Thr Ala Lys Ile Glu Ile Lys Ala Ser Leu Asp Gly Leu Glu Ile Asp
            50                  55                  60

Val Pro Gly Ile Asp Thr Asn Ala Cys His Phe Met Lys Cys Pro Leu
65                  70                  75                  80

Val Lys Gly Gln Gln Tyr Asp Ala Lys Tyr Thr Trp Asn Val Pro Lys
                85                  90                  95

Ile Ala Pro Lys Ser Glu Asn Val Val Val Thr Val Lys Leu Val Gly
                100                 105                 110

Asp Asn Gly Val Leu Ala Cys Ala Ile Ala Thr His Ala Lys Ile Asp
                115                 120                 125
```

Asp (2) INFORMATION FOR SEQ ID NO:23:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..387

(xi) SEQUENCE DESCRIPTION: SEQ ID NO:23:

```
GAT CAA GTC GAT GTT AAA GAT TGT GCC AAC AAT GAA ATC AAA AAA GTA        48
Asp Gln Val Asp Val Lys Asp Cys Ala Asn Asn Glu Ile Lys Lys Val
130             135                 140                 145

ATG GTC GAT GGT TGC CAT GGT TCT GAT CCA TGC ATC ATC CAT CGT GGT        96
Met Val Asp Gly Cys His Gly Ser Asp Pro Cys Ile Ile His Arg Gly
            150                 155                 160

AAA CCA TTC ACT TTG GAA GCC TTA TTC GAT GCC AAC CAA AAC ACT AAA       144
Lys Pro Phe Thr Leu Glu Ala Leu Phe Asp Ala Asn Gln Asn Thr Lys
        165                 170                 175

ACC GCT AAA ATT GAA ATC AAA GCC AGC CTC GAT GGT CTT GAA ATT GAT       192
Thr Ala Lys Ile Glu Ile Lys Ala Ser Leu Asp Gly Leu Glu Ile Asp
    180                 185                 190

GTT CCC GGT ATC GAT ACC AAT GCT TGC CAT TTT ATG AAA TGT CCA TTG       240
Val Pro Gly Ile Asp Thr Asn Ala Cys His Phe Met Lys Cys Pro Leu
195                 200                 205

GTT AAA GGT CAA CAA TAT GAT GCC AAA TAT ACA TGG AAT GTG CCG AAA       288
Val Lys Gly Gln Gln Tyr Asp Ala Lys Tyr Thr Trp Asn Val Pro Lys
210                 215                 220                 225

ATT GCA CCA AAA TCT GAA AAC GTT GTC GTT ACA GTC AAA CTT GTT GGT       336
Ile Ala Pro Lys Ser Glu Asn Val Val Val Thr Val Lys Leu Val Gly
            230                 235                 240

GAT AAT GGT GTT TTG GCT TGC GCT ATT GCT ACC CAC GCT AAA ATC AAA       384
Asp Asn Gly Val Leu Ala Cys Ala Ile Ala Thr His Ala Lys Ile Lys
        245                 250                 255

GAT TAA                                                               390
Asp
```

(2) INFORMATION FOR SEQ ID NO:24:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO:24:

```
Asp Gln Val Asp Val Lys Asp Cys Ala Asn Asn Glu Ile Lys Lys Val
 1               5                  10                  15

Met Val Asp Gly Cys His Gly Ser Asp Pro Cys Ile Ile His Arg Gly
            20                  25                  30

Lys Pro Phe Thr Leu Glu Ala Leu Phe Asp Ala Asn Gln Asn Thr Lys
        35                  40                  45

Thr Ala Lys Ile Glu Ile Lys Ala Ser Leu Asp Gly Leu Glu Ile Asp
    50                  55                  60
```

```
Val Pro Gly Ile Asp Thr Asn Ala Cys His Phe Met Lys Cys Pro Leu
 65                  70                  75                  80

Val Lys Gly Gln Gln Tyr Asp Ala Lys Tyr Thr Trp Asn Val Pro Lys
             85                  90                  95

Ile Ala Pro Lys Ser Glu Asn Val Val Thr Val Lys Leu Val Gly
            100                 105                 110

Asp Asn Gly Val Leu Ala Cys Ala Ile Ala Thr His Ala Lys Ile Lys
            115                 120                 125

Asp
```

(2) INFORMATION FOR SEQ ID NO:25:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..387

(xi) SEQUENCE DESCRIPTION: SEQ ID NO:25:

```
GAT CAA GTC GAT GTT AAA GAT TGT GCC AAC AAT GAA ATC AAA AAA GTA     48
Asp Gln Val Asp Val Lys Asp Cys Ala Asn Asn Glu Ile Lys Lys Val
130             135                 140                 145

ATG GTC GAT GGT TGC CAT GGT TCT GAT CCA TGC ATC ATC CAT CGT GGT     96
Met Val Asp Gly Cys His Gly Ser Asp Pro Cys Ile Ile His Arg Gly
                150                 155                 160

AAA CCA TTC ACT TTG GAA GCC TTA TTC GAT GCC AAC CAA AAC ACT AAA    144
Lys Pro Phe Thr Leu Glu Ala Leu Phe Asp Ala Asn Gln Asn Thr Lys
            165                 170                 175

ACC GCT AAA ATT GAA ATC AAA GCC AGC CTC GAT GGT CTT GAA ATT GAT    192
Thr Ala Lys Ile Glu Ile Lys Ala Ser Leu Asp Gly Leu Glu Ile Asp
        180                 185                 190

GTT CCC GGT ATC GAT ACC AAT GCT TGC CAT TTT ATG AAA TGT CCA TTG    240
Val Pro Gly Ile Asp Thr Asn Ala Cys His Phe Met Lys Cys Pro Leu
    195                 200                 205

GTT AAA GGT CAA CAA TAT GAT GCC AAA TAT ACA TGG AAT GTG CCG AAA    288
Val Lys Gly Gln Gln Tyr Asp Ala Lys Tyr Thr Trp Asn Val Pro Lys
210                 215                 220                 225

ATT GCA CCA AAA TCT GAA AAC GTT GTC GTT ACA GTC AAA CTT GTT GGT    336
Ile Ala Pro Lys Ser Glu Asn Val Val Thr Val Lys Leu Val Gly
                230                 235                 240

GAT AAT GGT GTT TTG GCT TGC GCT ATT GCT ACC CAC GCT AAA ATC CGT    384
Asp Asn Gly Val Leu Ala Cys Ala Ile Ala Thr His Ala Lys Ile Arg
            245                 250                 255

AAT TAA                                                             390
Asn
```

(2) INFORMATION FOR SEQ ID NO:26:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO:26:

Asp Gln Val Asp Val Lys Asp Cys Ala Asn Asn Glu Ile Lys Lys Val

```
  1               5              10              15
Met Val Asp Gly Cys His Gly Ser Asp Pro Cys Ile Ile His Arg Gly
                         20              25              30

Lys Pro Phe Thr Leu Glu Ala Leu Phe Asp Ala Asn Gln Asn Thr Lys
                 35              40              45

Thr Ala Lys Ile Glu Ile Lys Ala Ser Leu Asp Gly Leu Glu Ile Asp
         50              55              60

Val Pro Gly Ile Asp Thr Asn Ala Cys His Phe Met Lys Cys Pro Leu
 65              70              75                          80

Val Lys Gly Gln Gln Tyr Asp Ala Lys Tyr Thr Trp Asn Val Pro Lys
                         85              90              95

Ile Ala Pro Lys Ser Glu Asn Val Val Val Thr Val Lys Leu Val Gly
                100             105             110

Asp Asn Gly Val Leu Ala Cys Ala Ile Ala Thr His Ala Lys Ile Arg
                115             120             125

Asn
```

(2) INFORMATION FOR SEQ ID NO:27:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

GCCATATGGA TCAAGTCGAT GCTAAAGAGT GTGC                  34

(2) INFORMATION FOR SEQ ID NO:28:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

GCCATATGGA TCAAGTCGAT GCTAAAAATT GTGC                  34

(2) INFORMATION FOR SEQ ID NO:29:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

GCCATATGGA TCAAGTCGAT GTTAAAAAAT GTGC                  34

(2) INFORMATION FOR SEQ ID NO:30:

(i) SEQUENCE CHARACTERISTICS:
        (A) LENGTH: 19 base pairs
        (B) TYPE: nucleic acid
        (C) STRANDEDNESS: single
        (D) TOPOLOGY: linear

```
    (ii) MOLECULE TYPE: cDNA (xi) SEQUENCE DESCRIPTION: SEQ ID NO:30:

CATTGTTGGG ACAATCTTT                                              19

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

GTGGCAACCT TCCACCATTA C                                           21

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

GTGGCAACCG TTGACCATTA C                                           21

(2) INFORMATION FOR SEQ ID NO:33:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

CCGTGGCAAC CTTTGACCAT TAC                                         23

(2) INFORMATION FOR SEQ ID NO:34:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

CGAAGCTTAA TCATCGATTT TAG                                         23

(2) INFORMATION FOR SEQ ID NO:35:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:
```

```
CGAAGCTTAA TCTTTGATTT T                                                    21
```

(2) INFORMATION FOR SEQ ID NO:36:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

```
CGAAGCTTAA TTACGGA                                                         17
```

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

```
ATCAAGCTGG GATTTAGGTG                                                      20
```

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

```
CCCCGCGCGT TGGCCGATTC                                                      20
```

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

```
GCCCGGGAGT TCTCGATCCC                                                      20
```

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

```
CCGATTCATT AATGCAGCCC                                                      20
```

ENGINEERED ACARID ALLERGEN AND PROCESS FOR PRODUCING THE SAME

BACKGROUND OF THE INVENTION

1. Field of the Invention

Figure 1:
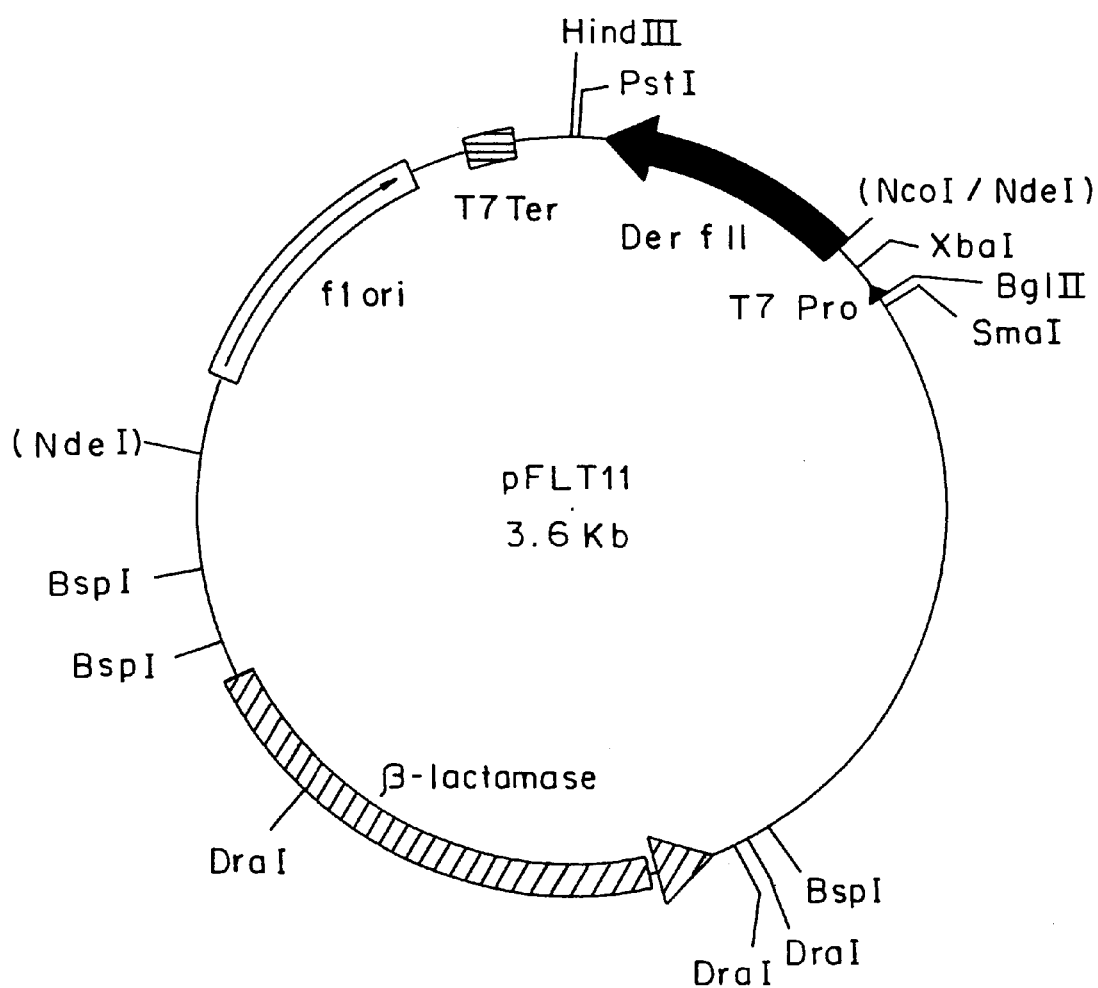

The present invention relates to a modified allergen, which is obtained by altering a major allergen (Der f II) of house dust mites by gene engineering, and to a method for production of the modified allergen. The modified allergen obtained by the production method can be utilized as a medicine for treating allergic diseases.

2. Description of the Related Art

It is considered that many allergic diseases are due to several kinds of symptoms which are developed by sensitization to the antigen causing the diseases, in which an IgE antibody specific for an allergen in blood serum and tissue is produced, and when the antibody is exposed again to the antigen, the antibody reacts with the antigen in each tissue. Particularly, an immediate type reaction is caused by the combination of antigens with IgE antibodies on mast cells and basophils followed by cross-linking the IgE antibodies, and the subsequent release of several kinds of chemical mediators from mast cells or basophils.

There is a method for controlling the binding between the antigen and the IgE antibody as a method for treating allergic diseases. If the binding between the antigen and the IgE antibody is controlled, the cross-linking among the IgE antibodies on mast cells or basophils, and the release of chemical mediators are controlled to have an effect on the treatment.

On the other hand, it appears that allergic diseases, such as bronchial asthma, childhood asthma, atopic dermatitis and the like, are mainly caused by an allergen from mites living in house dust. Several kinds of proteins of major mite allergens have been identified as major mite allergens (Platts-Mills et al., J. Allergy Clin. Immunol., 80, 755; 1987). Furthermore, a method for mass producing a purified major mite allergen has been disclosed (Yuuki et al., Japanese J. Allergology, 39, 557 (1990) and Japanese Patent Application No. 3-254683). In addition, the allergen in which a part of the above purified major mite allergen is changed, and a production method thereof has been filed (Japanese Patent Application No. 5-139793).

However, the proteins of the major allergens of mites which have been reported and identified show problems of an allergic reaction, namely anaphylactic shock, in hyposensitization therapy, because the activity of these allergens is high.

On the other hand, if the modified major mite allergen, which has lower IgE-binding activity or lower allergen activity than wild-type allergens and inhibits the binding of the antigen (Der f II) and the IgE antibody, is obtained, it is possible to provide an effective medicine for treating allergic diseases. The medicine does not show the anaphylactic shock of an allergic reaction caused by antigen administration, and it does not have an effect on the other parts of the immune system since the medicine is specific to the antigen. Modified major mite allergens have been disclosed in Japanese Patent Application Nos. 5-139793 and 5-275897. In the former application, there are problems of maintenance and stability of immunogenicity because the molecular structure is greatly changed by amino acid substitutions. In the latter application, it is not enough to minimize the structural change and to lower the allergen activity because a modified position of the allergen is not satisfactorily specified, and only alanine is used as a substitute amino acid.

SUMMARY OF THE INVENTION

The inventors of the present invention have found that, when an amino acid of a specified part of the major mite allergen Der f II, which is already disclosed, is replaced with other similar amino acids to minimize the structural change, it has been found that IgE-binding activity can be changed. It is found that there is no difference between the modified major mite allergens and those of a wild-type as to the activity that inhibits the antigen (Der f II) from binding to IgE.

An object of the present invention is to provide a method for mass producing the modified major mite allergen Der f II in which amino acid replacements are introduced by gene engineering. Namely, the present invention aims to produce a material which can be utilized as a medicine for treating allergic diseases.

The present invention involves a method in which a major allergen (Der f II) of house dust mites (*Dermatophagoides farinae*) is modified by gene engineering to replace amino acid residues with other amino acid residues, prokaryotic or eukaryotic host cells, transformed with a replication vector containing a gene which encodes the modified major mite allergen, Der f II, are cultured, and the modified major mite allergen is obtained from the culture.

BRIEF DESCRIPTION OF THE DRAWINGS

FIG. 1 shows pFLT11 which was used for amplification by a PCR method.

FIG. 2 is a graph showing the results that the absorbance of the reaction solution observed at 420 nm in Example 2, and evaluated the value as binding activities of modified proteins D7K (SEQ ID NO:11), D7E (SEQ ID NO:8), D7N (SEQ ID NO:10), D19E (SEQ ID NO:16), D19N (SEQ ID NO:18), R128D (SEQ ID NO:22), R128K (SEQ ID NO:24), and D129N (SEQ ID NO:26) of Der f II and human IgE. The amino acid sequences presented at the bottom of the panels correspond to amino acid residues 1–21 of SEQ ID NO:2 (left panel) and amino acid residues 114–129 of SEQ ID NO:6 (right panel).

DETAILED DESCRIPTION OF THE INVENTION

It has been disclosed that the major mite allergen Der f II has six cysteine residues and has three intramolecular cross-linkages (between the 8th and 119th, between 21st and 27th, and between 73rd and 78th amino acid residues) by disulfide bonds (Nishiyama et al., International Archives of Allergy and Immunology, 101, 159, 1993). Further, the effect of IgE-binding activities is disclosed by preparing a modified Der f II which is obtained by removing one of those disulfide bonds in the molecule by gene engineering techniques (Japanese Patent Application No. 5-139793). According to the report, the disulfide bond between the 8th and 119th amino acid residues is the most important for IgE-binding activity.

The present inventors have repeatedly investigated and found that an area around the disulfide bond between the 73rd cysteine and 78th cysteine has an effect on IgE-binding. Moreover, they have found that it is possible to lower the IgE-binding capability significantly by replacing one amino acid with another amino acid having a very similar property. For example, the 7th aspartic acid residue can be replaced with glutamic acid or asparagine, as well as the above-mentioned alanine. Though the 19th aspartic acid residue is replaced with glutamic acid, a change in the IgE-binding capability is not observed. However, when the aspartic acid residue is replaced with asparagine, it is found that the IgE-binding capability is reduced, and the capability is affected by the electric charge at the 19th amino acid residue. In addition, for example, when the 9th alanine residue is replaced with leucine, the binding activity is about 30% of the original activity. On the other hand, when the alanine residue is replaced with proline, as shown in the present invention, it is found that the binding activity is lowered to 10% or less. Among the mutants having reduced binding activity, effective mutants are found by an animal experiment with mice that develop mite allergy. The present invention has been attained by finding modified allergens effective for a hyposensitization treatment of patients with mite allergy.

The modified allergens of the present invention can be produced by any method suitable to the aims of the present invention, and preferably by a site-directed mutagenesis method. Although many site-directed mutagenesis methods have been established, a PCR method is readily available (Ito et al., Gene, 102, 67, 1991). As an example, it is shown in the following that the 7th aspartic acid residue of the Der f II protein (SEQ ID NO:2) is replaced with a glutamic acid residue using the DNA chain as shown in SEQ ID NO:1.

The codon corresponding to the 7th aspartic acid residue of SEQ ID NO:8 is GAT in SEQ ID NO:7. This codon is replaced with a codon corresponding to the glutamic acid residue, for example, GAG. The oligonucleotide having the same sequence as that of the DNA sequence near the aspartic acid residue, in which only the codon (GAT) of the aspartic acid residue is replaced with a codon (GAG) of the glutamic acid residue, is synthesized (Table 1, F-D7E). This synthesis may be conducted by any well-known method, such as conveniently performed by an automated synthesizer (for example, the Model 381 DNA synthesizer; manufactured by Applied Biosystems).

Any DNA fragment, including the cDNA of Der f II shown in SEQ ID NO:7, can be used as the template DNA for PCR amplification. In this case, pFLT11 (FIG. 1) was used as the template. The synthetic oligonucleotide R1 (Table 1) has the same sequence as that of the region containing a Hind III recognition sequence downstream of the Der f II-coding region on pFLT11, and PCR was conducted using the above two synthetic oligonucleotides F-D73 and R1 as primers.

After the PCR amplification, the nucleotide sequences of the resulting amplified DNA fragments can be determined by the dideoxy method (J. Mol. Biol. 162, 729–773, 1982) and the like.

Thus, modified DNA, in which the introduction of a mutation has been confirmed, is inserted into a cloning site of a suitable expression vector, and a modified Der f II is expressed. In this expression, any plasmid vector stably maintained in E. coli can be used; for example, pGEMEX1 (manufactured by Promega Company) can conveniently be used. In this vector, a T7 promoter is used as a high expression promoter, and the recombinant protein is accumulated in E. coli as inclusion bodies. Many methods can be used in a chain of these operations (Maniatis et al, Molecular Cloning, Cold Spring Harbor Laboratory, 1982).

The DNA can be expressed by using a suitable vector, such as YEp13 (Broach et al, Gene, 8, 121–133, 1979) in yeast. Using a yeast vector having an expression cassette in combination with a modified Der f II gene which is obtained by the method of the present invention, a suitable yeast cell can be transformed. In order to accomplish this object, the DNA sequence of the present invention must not be controlled by an E. coli promoter, but rather by an eukaryotic promoter, for example, delta P8 and the like (Otake et al., Agric. Biol. Chem., 52, 2753–2762, 1988).

Thus, modified plasmids were prepared by substituting amino acids, other than alanine, for the 7th, 9th, 19th, 128th and 129th amino acid residues from the N terminus of the major mite allergen Der f II, and each plasmid was used to transform E. coli and express a modified major mite allergen.

The IgE antibody binding activity of modified Der f II was then quantitatively determined. Prior to this determination, each of the modified Der f II proteins needed to be purified as follows. Cells of host E. coli BL 21 carrying the above plasmid were harvested after expression. The cells were hypersonically crushed, and the Der f II protein, expressed as an inclusion body, was collected by centrifugation. After dissolving the inclusion body with 6M urea, the solution was dialyzed to a buffer of 20 mM Tris Hcl (pH 8.5) to remove urea and refold the protein. Then, the Der f II fraction was purified by anion exchange chromatography, i.e., the fraction including the refolded protein was adsorbed to a DEAE-Toyopearl (manufactured by Tosoh) column and eluted with 80 mM NaCl to obtain the purified Der f II protein.

Using the resulting pure modified Der f II protein, the IgE-binding activity was quantitatively determined. To accomplish this object, a RAST-EIA kit (manufactured by Pharmacia) was conveniently used. First, a disk of filter paper activated with bromcyanide was immersed in 50 µl of a solution of modified Der f II, which was diluted with a buffer solution of 0.1 M boric acid (pH 8.5), and was permitted to stand overnight, where the protein became bound to the filter paper. After washing, the filter paper was immersed in 50 µl of a serum from a patient allergic to mites, which serum was diluted four times with a buffer solution enclosed with the kit, allowed to stand for two hours at 37° C., and the antigen, bound to the filter paper, was then bound to human anti-Der f II IgE antibodies in the serum. The reaction was then allowed to proceed in accordance with the reaction protocol of the kit. After all reaction was finished, the absorbance of the sample at 420 nm was used as an index of IgE-binding activity, with the results being shown in FIG. 2. Modified proteins obtained by substituting alanine, asparagine and glutamic acid for the 7th and 19th aspartic acid residues are noted. As to the 7th aspartic acid residue, even if it is replaced by any other amino acid, the IgE-binding ability is reduced in comparison with that of the wild-type Der f II. Accordingly, the necessary condition for IgE-binding is that the 7th amino acid residue be aspartic acid. On the other hand, as to the 19th aspartic acid residue, if it is replaced by alanine and glutamine, then the binding ability is greatly reduced; but if it is replaced by glutamic acid, the binding ability is slightly reduced. From these results, it is considered that, for IgE-binding, it is necessary that an acidic amino acid be at that position. For the 9th alanine residue, the binding activity of the compound in which the 9th alanine residue is substituted with leucine is reduced to about 30% in comparison with the original binding activity of wild-type Der f II, and the binding activity of the compound in which the 9th alanine residue is replaced by proline is reduced to 10% or less. As a result, it is found that the replacement of an amino acid, which greatly contributes to the change in constitution of the protein, reduces the binding activity.

Using the modified proteins of Der f II having a lowered IgE-binding activity in an animal experiment, the efficiency for hyposensitization was confirmed. 10 μg of Der f II and 100 μg of Freund's adjuvant were intraperitoneally administered to male seven-week-old A/J mice to sensitize with rDer f. One mg/ml of modified proteins were intranasally administered to sensitized mice two times a week for three weeks. The same amount of a physiological salt solution was administered to the controls. One week after the final administration, the mice were placed into a chamber for small animals to inhale five mg/ml of nebulized Der f II for 30 minutes. After 24 hours, the mice were killed by bleeding, followed by bronchial alveolar lavage with 1 ml of PBS. Cytospin preparations were made from 200 μl of bronchial alveolar lavage fluid (abbreviated as BALF hereinafter), and stained with DIF-QUICK. The samples were observed under a microscope at 400 magnification, and leukocytes (macrophages, neutrophils, eosinophils and lymphocytes) were counted within the range of the microscope to determine the degree of airway inflammation. In non-sensitized mice, except for macrophages, leukocytes in BALF taken after inhalation of the antigen, are rarely observed. On the other hand, in immunized mice, many neutrophils and lymphocytes were observed, and the leukocyte count was about 2.5 times higher than that of the non-immune groups. In sensitized mice, it was confirmed that the airway inflammation was induced by the inhalation of the antigen. In contrast, in sensitized mice which were administered either wild-type Der f II or the substituent, the leukocyte count was substantially reduced, showing effective hyposensitization. Accordingly, it is proven that modified proteins of Der f II are safe and effective agents for treating allergic diseases, because there is little possibility of anaphylactic shock with the reduced IgE-binding activity.

Best Mode for Carrying Out the Invention

The following examples illustrate the present invention in details.

Example 1

Construction of an Expression Vector of a Der f II Amino Acid-substituted Mutant A factor developing a variant in which the targeted amino acid residue of Der f II had been substituted by a different amino acid was prepared by a site-directed mutagenesis method of PCR. Before conducting the PCR method, oligonucleotides were synthesized as shown in Table 1.

TABLE 1

Base sequences of synthesized oligonucleotides for preparing mutants

| Oligonucleotides (Mutants) | Sequences* NdI |
|---|---|
| F-D7E(Asp7Glu) | 5'-GC<u>CATATG</u>GATCAAGTCGATGCTAAAGAGTGTGC-3'<br>SEQ ID NO: 27 |
| F-D7N(Asp7Asn) | 5'-GC<u>CATATG</u>GATCAAGTCGATGCTAAAAATTGTGC-3'<br>SEQ ID NO: 28 |
| F-D7K(Asp7Lys) | 5'-GC<u>CATATG</u>GATCAAGTCGATGTTAAAAATGTGC-3'<br>SEQ ID NO: 29 |
| R-A9P(Ala9Pro) | 5'-CATTGTTGGGACAATCTT-3'<br>SEQ ID NO: 30 |
| R-D19E(Asp19Glu) | 5'-GTGGCAACCTTCGACCATTAC-3'<br>SEQ ID NO: 31 |
| R-D19N(Asp19Asn) | 5'-GTGGCAACCGTTGACCATTAC-3'<br>SEQ ID NO: 32 |
| R-D19K(Asp19Lys) | 5'-CCGTGGCAACCTTTGACCATTAC-3'<br>SEQ ID NO: 33 |
| R-128D(Arg128Asp) | 5'-CG<u>AAGCTT</u>AATCATCGATTTTAG-3'<br>SEQ ID NO: 34 |
| R-R128K(Arg128Lys) | 5'-CG<u>AAGCTT</u>AATCTTTGATTTT-3'<br>SEQ ID NO: 35 |
| R-D129N(Asp129Asn) | 5'-CG<u>AAGCTT</u>AATTACGGA-3'<br>SEQ ID NO: 36<br>Hind III |
| R1 | 5'-ATCAAGCTGGGATTTAGGTG-3'<br>SEQ ID NO: 37 |
| F1 | 5'-CCCCGCGCGTTGGCCGATTC-3'<br>SEQ ID NO: 38 |
| F2 | 5'-GCCCGGG<u>AGTTCT</u>CGATCCC-3'<br>SEQ ID NO: 39 |

TABLE 1-continued

Base sequences of synthesized oligonucleotides for preparing mutants

| Oligonucleotides (Mutants) | Sequences* NdI |
|---|---|
| F3 | ΔBgl II<br>5'-CCGATTCATTAATGCAGCCC-3'<br>SEQ ID NO: 40 |

*: Boldface shows mismatching of amino acid substituents, and underlines show recognition sites of restriction enzymes.

When the 7th Asp residue from the N terminus of Der f II was varied to Glu or Asn, a synthesized oligonucleotide was designed so as to have the same sequence as that of wild-type Der f II, except that a codon for the targeted amino acid to be substituted was changed to a codon for Glu or Asp, and so as to reintroduce a recognition sequence of restriction enzyme Nde I into an upstream region of the initiation codon. PCR was carried out using the expression vector pFLT11 (Japanese Patent Application No. 5-139793) which includes the cDNA of the wild-type Der f II as a template. The synthesized oligonucleotide R1, having a sequence complementary to a region containing a Hind III recognition sequence downstream of the site in which Der f II is cloned into pFLT11, and the above-synthesized oligonucleotide F-D7E or F-D7N were used as primers. The PCR solution was prepared by adding: (a) one μg each of two primers, F-D7E and R1, or F-D7N and R1, to one ng of the plasmid pFLT11 as a template; (b) 10 μl of a 10× reaction solution attached to Taq DNA polymerase (TOYOBO), 10 μl of a 25 mM MgCl$_2$ solution; (c) dATP, dCTP, dGTP and dTTP so that each final concentration is 200 μM in 100 μl of the reaction solution; (d) distilled water to adjust the volume of the reaction solution to 100 μl; and (e) 2.5 units of the Taq DNA polymerase. After the resulting solution was left at 94° C. for one minute to change the double-stranded DNA of the template into a single-stranded DNA, it was left at 37° C. for two minutes to anneal the primer into a single-stranded template, and then the solution was reacted at 72° C. for three minutes to synthesize a complementary DNA by the polymerase. The above steps were repeated 25 cycles to amplify the objective DNA fragments.

After the digestion of the resulting DNA fragments by Nde I and Hind III, the fragments were inserted into the Nde I/Hind III site of plasmid pGEME1-Δ Nde (Japanese Patent Application No. 5-139793) to obtain expression vectors carrying the DNAs (SEQ ID NO:13 and SEQ ID NO:17) of the mutants, pFLT11-D7E and D7N, respectively. On the other hand, when the 9th and 19th amino acid residues were substituted, the following two-part PCR was performed. Namely, synthesized nucleotides R-A9P and R-D19N, having the same sequences as that of wild-type Der f II except for the codon for the targeted amino acid residues to be changed as shown in Table 1, were prepared. The PCR reaction was conducted using any one of those synthesized nucleotides as a primer, synthesized nucleotide F1 having the same sequence as that of the sequence about 40 bps upstream from the Bgl II site of pFLT11 as another primer, and pFLT11 as a template. At the same time, a second PCR reaction was conducted using F2, which was designed so as to be a sequence in which it is impossible to cleave the Bgl II site on pFLT11 with the same enzyme as a primer, the above R1 as another primer, and pFLT11 as a template.

Each 10 ng of these two DNA fragments obtained by PCR was added to the solution obtained by removing the primer and the polymerase from the previous PCR solution. The mixture was reacted at 94° C. for 10 minutes, cooled gradually to 37° C. for 30 minutes, and maintained at 37° C. for 15 minutes to anneal these two fragments. Subsequently, 2.5 units of Taq polymerase was added, and maintained at 60° C. for 30 minutes, and maintained at 37° C. for 15 minutes to anneal these two fragments. Subsequently, 2.5 units of Taq polymerase was added and maintained at 60° C. for three minutes to elongate these two DNA fragments. Then, each of 0.5 μg of the previous two primers R1 and F1 were added, and 20 cycles of PCR were repeated to amplify these fragments. By such an operation, two kinds of fragments having the same length were obtained. One fragment had a Bgl II recognition sequence, and it was varied at the targeted amino acid residue. The other fragment had the same amino acid sequence as that of wild type, and it was varied so as to be impossible to be cleaved at the Bgl II recognition sequence. After these fragments were digested with Bgl II and Hind III, they were ligated to pGEMEX1-Δ Nde I treated with Bgl II and Hind III. The only vectors that were obtained were those in which the targeted mutations were introduced. Expression vectors pFLT11 -A9P and pFLT11 -D19N carrying cDNA (SEQ ID NO:13 and SEQ ID NO:17) of the Der f II mutants, in which the 9th and 19th amino acid residues were substituted by Pro (SEQ ID NO:14) and Asn (SEQ ID NO:18), were prepared.

For the construction of the Der f II mutants R128D (SEQ ID NO:22, R128K (SEQ ID NO:24) and D129N (SEQ ID NO:26), in which the 128th and 129th amino acid residues were substituted with nucleotide sequences corresponding to SEQ ID NOs:21, 23 and 25, respectively, the same PCR method as that used for substituting the 7th amino acid resideue was used. In this case, using primers of a combination of each R-R128D, R-R128K or R-D129N and F3 having the same sequence as that of a sequence about 130 bps upstream from the initiation codon of Der f II, a PCR reaction was carried out under the same conditions as for D7E and the like. The PCR products were digested with Bgl II and Hind III by the same method as that of A9P and the like for insertion into pGEMEX1-Δ Nde I.

Example 2

Comparison of IgE-binding Abilities of the Amino Acid Substituted Mutants of Der f II by a RAST-EIA Method After *E. coli* BL21 was transformed by each expression vector of the Der f II mutants constructed in Example 1 (pFLT11-D7E, pFLT11-D7N, pFLT11-A9P, and pFLT11-D19N) and grown on an agar medium containing ampicillin (1% BACTOTRYPTONE, 0.5% yeast extract, 0.5% NaCl, 1.5% BACTOAGAR (these units werew/v), 50 µg/ml ampicillin, pH 7.4), the resulting colonies were inoculated into 5 ml of an L liquid medium containing ampicillin (agar was removed from the L agar medium containing ampicillin). After the colonies were cultivated with shaking at 30° C. overnight, the medium was added to 500 ml of an L liquid medium containing ampicillin, and the solution was further cultivated with shaking at 30° C. When the absorbancy of the solution reached 0.4, isopropyl-β-thiogalactopyranocide (IPTG) was added to 0.1 mM, and the solution was cultivated for more five hours with shaking, with the protein being expressed. Then, the *E. coli* BL21 cells, expressing each Der f II mutant, were harvested by centrifugation, the cells were broken with a ultrasonic blender, and the Der f II mutants, expressed as inclusion bodies, were collected by centrifugation. The inclusion bodies were refolded by solubilization in a buffer solution containing urea (6M urea, 100 mM Tris HCl and 10 mM ethylenediamine tetraacetic acid (EDTA), pH 7.5), and by dialysis in a Tris buffer solution (20 mM TrisHCl, pH 8.5). This solution was provided on an ion exchange column DEAE-Toyopearl (TOSOH) which was equilibrated in the above Tris buffer solution and eluted by a concentration gradient of NaCl (from 0 mM to 100 mM). The fragment eluted at about 80 mM of salt concentration was subjected to SDS-PAGE, and a purified sample was obtained as a single band of about 14,000 of molecular weight.

Human IgE-binding activity of the wild-type Der f II and each mutant was determined by using a RAST-EIA kit manufactured by Pharmacia. The method was performed as follows. First, a filter paper, which was activated with bromocyanide, was dipped in 50 µl of an antigen solution diluted with a buffer solution of 0.1 M boric acid (pH 8.5), and incubated overnight at room temperature to adsorb the antigen. The antigen solution was removed, then the filter paper was washed in 500 µl of a solution of 0.1 M sodium hydrogencarbonate, dipped in 250 µl of 1 M β-ethanolamine (pH 9.0), and incubated for three hours at room temperature to prevent non-specific absorption on the paper by the blocking operation. The ethanolamine solution was removed, the paper was washed once in 500 µl of a solution of 0.1 M sodium hydrogencarbonate, three times in 500 µl of the buffer solution of 0.1M sodium acetate (pH 4.0), and twice in 500 µl of the buffer solution enclosed with the kit. 50 µl of serum from an allergy patient, which was diluted 4 times with the buffer solution enclosed with the kit, was added, and the paper in the solution was incubated for two hours at 37° C. to combine anti-Der f II-IgE in the serum with the antigen adsorbed on the filter paper.

Figure 2:
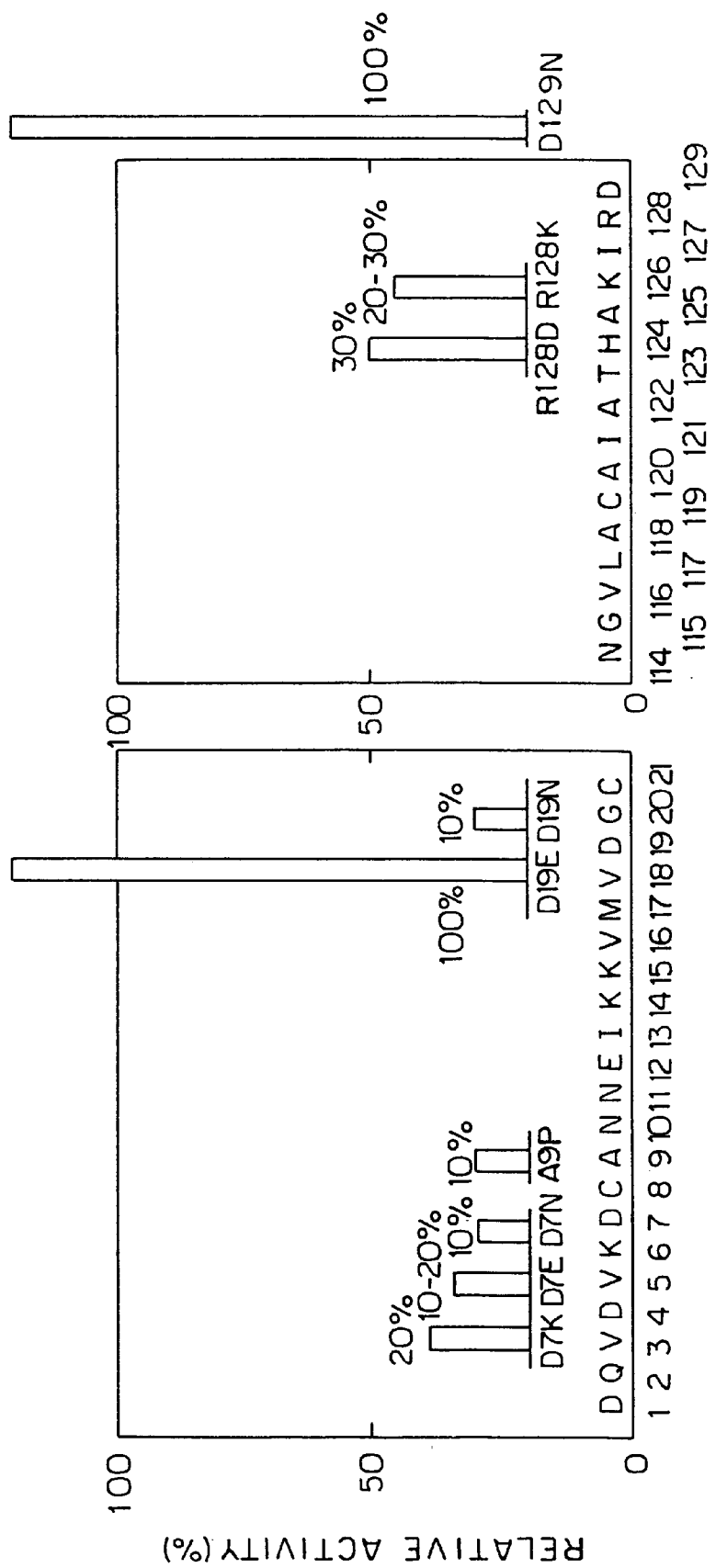

After the antigen-antibody reaction, the serum was removed, the filter paper was washed three times by dipping it for ten minutes in 2.5 ml of the washing solution enclosed with the kit, 50 µl of an anti-human IgE-rabbit IgG solution labeled with β-D-galactosidase in the kit was added, and the resulting solution was left for 16–20 ours at room temperature to combine the IgE adsorbed to the antigen. After the enzyme-labeled antibody solution was removed, the filter paper was washed as described above, and 200 µl of a substrate o-nitrophenol-β-D-galactopyranoside enclosed with the kit was added to react at 37° C. for two hours. After adding 2 ml of a solution enclosed with the kit for stopping the enzyme reaction, the absorbance at 420 nm of the reaction solution was determined, and the value was evaluated as the binding activity of Der f II and human IgE. The results are shown in FIG. 2. It is recognized that the IgE-binding activity of each Der f II mutant of D7E, D7N, A9P and D19N is remarkably reduced in comparison with the wild-type Der f II. For example, if amino acid residue Asp 7 or Asp 19, which are considered to be important for forming a human IgE epitope of Der f II based on the experiment substituting Ala therefor, was replaced with Asn which does not have a negative charge unlike Asp, it was found that the IgE-binding activity was remarkably reduced like the Ala-substituted Der f II. As for the Asp 7 residue, even if it was replaced with Glu, which is an amino acid having negative charge like Asp, the IgE-binding activity was also reduced. Moreover, by substituting Pro having a different side group from Ala 9, which might be in a recognition site of Der f II or adjacent to the site, a variant having strictly lower IgE-binding activity than that of the mutant A9L (the mutant in which Leu is substituted for Ala 9) was successfully made.

Example 3

A Test for Evaluating the Effectiveness in the Hyposensitization Treatment of the Amino Acid Substituted Mutant of Der f II Materials and Methods Immunization Ten µg of recombinant Der f II (abbreviated as rDer f II hereinafter) and 100 µl of Freund's adjuvant were intraperitoneally administered three times to 24 seven-week-old male A/J mice every two weeks.

Test Groups

The 24 immunized mice were divided into a control group of six mice, a rDer f II administration group of six mice, a D7N administration group of six mice, and a D19N administration group of six mice. In addition, as a reaction-negative control group, three mice, which were not immunized, were designated as a non-immune group. Administration of rDer f II and mutants substituted by amino acid residues (D7N and D19N)

Two weeks after the final immunization, 20 µ of each of the following were intranasally administered twice a week for a period of three weeks: a physiological salt solution of phosphoryic acid buffer (abbreviated as PBS hereinafter) to the control group, one mg/ml of rDer f II to the rDer f II administration group, one mg/ml of D7N to the D7N administration group, and one mg/ml of D19N to the D19N administration group. The non-immune group was not treated.

A Test for Provoking Late-phase Airway Inflammation

A week after the final intranasal administration, the mice were placed into a chamber for small animals to inhale five mg/ml of nebulized Der f II for 30 minutes. After 24 hours, the mice were killed by bleeding, followed by bronchialalveolar lavage with 1 ml of PBS. Cytospin preparations were made from 200 µl of BALF, and stained with DIF-QUICK. The samples were observed under a microscope at 400 magnification, and leukocytes (macrophages, neutrophils, eosinophils and lymphocytes) were counted within the range of the microscope to determine the degree of airway inflammation.

Results

Number of Leukocytes in BALF After Inhaling rDer f II

For the non-immune group, except for macrophages, leukocytes in BALF were rarely observed. On the other hand, for the control group of immunized mice, many neutrophil and lymphocytes were observed. In comparison with non-immune groups, the leukocyte count of the control group was about 2.5 times higher. For example, in the case of the control group, it was confirmed that airway inflammation was provoked by the inhalation of the antigen. However, for the groups in which rDer f II or the mutants with substituted amino acid residues, D7N and D19N, were administered, the number of neutrophils and all leukocytes were decreased in comparison with the control group. It is clear that hyposensitization to rDer f II by the intranasal administration was achieved. The results are shown in Table 2.

TABLE 2

| | Number of leukocytes (± standard error) | | | |
|---|---|---|---|---|
| Test groups | Macrophage | Neutrophil | Eosinophil | Lymphocyte |
| Nonimmune | 43.2 ± 5.4 | 0.3 ± 0.3 | 0.0 | 0.2 ± 0.2 |
| Control | 47.1 ± 2.4 | 60.0 ± 13.5 | 1.7 ± 1.1 | 2.8 ± 1.3 |
| rDer fII | 42.7 ± 8.7 | 31.5 ± 8.9 | 3.7 ± 2.2 | 4.1 ± 1.4 |
| D7N | 46.8 ± 7.4 | 35.8 ± 10.5 | 2.9 ± 0.8 | 5.1 ± 3.0 |
| D19N | 45.9 ± 6.6 | 33.9 ± 7.7 | 3.0 ± 1.5 | 3.1 ± 1.7 |

Industrial Applicability

The modified Der f II made by gene technology according to the present invention can have reduced IgE-binding activity with a minimum of mutation (one amino acid in 129 amino acids) and can be utilized for safely treating each kind of allergy diseases caused by mites.

What is claimed is:

1. An isolated DNA molecule comprising a nucleotide sequence encoding a modified major mite allergen, wherein said nucleotide sequence is modified from nucleotide sequences SEQ ID NO:1, SEQ ID NO:3, or SEQ ID NO:5, encoding wild-type major mite allergen Derf II, to substitute a codon for a different amino acid residue other than alanine at a residue position selected from the group consisting of the $7^{th}$, $9^{th}$, $19^{th}$, $128^{th}$, and $129^{th}$ amino acid residue of wild-type major mite allergen Derf II.

2. The isolated DNA molecule according to claim 1, wherein said nucleotide sequence encodes a modified major mite allergen having an amino acid sequence selected from the group consisting of SEQ ID NOs:8, 10, 12, 14, 16, 18, 20, 22, 24 and 26.

3. The isolated DNA molecule according to claim 1, wherein said nucleotide sequence is selected from the group consisting of SEQ ID NOs:7, 9, 11, 13, 15, 17, 19, 21, 23 and 25.

4. A modified major mite allergen encoded by the isolated DNA molecule according to claim 1.

5. The modified major mite allergen according to claim 4, which has reduced IgE binding activity relative to a major mite allergen of SEQ ID NO:1, SEQ ID NO:3 or SEQ ID NO:5.

6. A pharmaceutical composition for treating mite allergic diseases or immunizing against mite allergic diseases, comprising the modified major mite allergen according to claim 4 and a pharmaceutically acceptable carrier.

* * * * *